Figure 1:
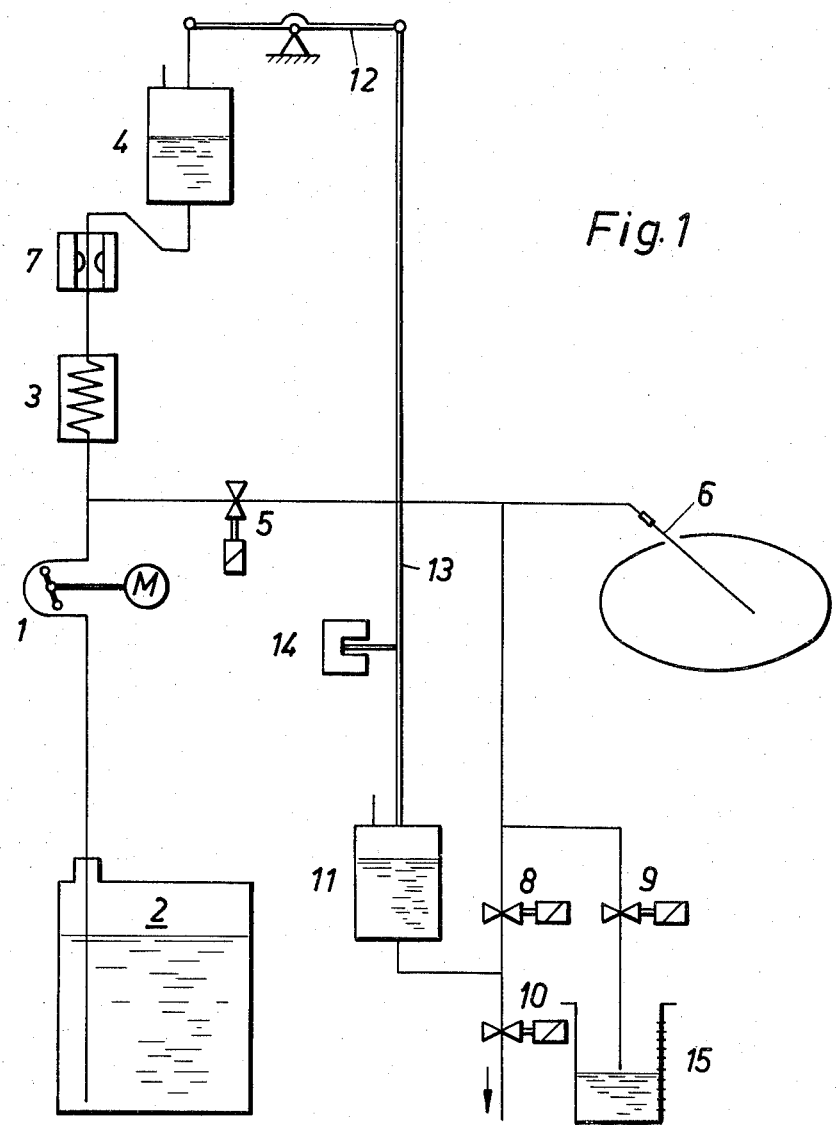

United States Patent [19]

Schael

[11] 4,240,408

[45] Dec. 23, 1980

[54] PERITONEAL DIALYSIS APPARATUS

[75] Inventor: Wilfried Schael, Bad Homburg, Fed. Rep. of Germany

[73] Assignee: Dr. Eduard Fresenius Chemisch-pharmazeutische Industrie KG, Apparatebau KG, Bad Homburg, Fed. Rep. of Germany

[21] Appl. No.: 966,498

[22] Filed: Dec. 4, 1978

[30] Foreign Application Priority Data

Dec. 10, 1977 [DE] Fed. Rep. of Germany ....... 2755214

[51] Int. Cl.³ .......................... A61B 19/00; A61J 7/00
[52] U.S. Cl. ................................ 128/1 R; 128/213 A
[58] Field of Search .............. 128/213, 213 A, 213 R, 128/214 R; 210/321 A, 321 B

[56] References Cited

U.S. PATENT DOCUMENTS 3,730,183 5/1973 Goldsmith et al. ............. 128/213 A

FOREIGN PATENT DOCUMENTS 2371931 7/1978 France ................................. 128/213 A Primary Examiner—Robert W. Michell
Assistant Examiner—T. J. Wallen
Attorney, Agent, or Firm—W. G. Fasse; D. F. Gould

[57] ABSTRACT

In peritoneal dialysis apparatus, flushing liquid is pumped into a supply vessel (4) which is then emptied into the body cavity through a valve (5) and a catheter (6). The supply vessel is then refilled while the cavity is drained back through the catheter into a receptacle (11) of the same weight and dimensions as the supply vessel. The supply vessel and receptacle are suspended at opposite ends of a balance beam (12) and when they are in balance after the receptacle has been filled, a valve (8) isolates the receptacle from the catheter and surplus fluid from the cavity is collected in a measuring vessel (15) through a valve (9), the receptacle being emptied through a valve (10).

3 Claims, 2 Drawing Figures

PERITONEAL DIALYSIS APPARATUS

BACKGROUND OF THE INVENTION

The invention relates to apparatus for carrying our peritoneal dialysis and measuring the amount of fluid which is withdrawn from the patient in such a process.

The usual process for peritoneal dialysis comprises introducing a given amount of a flushing fluid through a catheter which is inserted into the abdominal cavity of the patient, and then emptying the fluid subsequently, possibly after a given period of waiting. This process is repeated several times in the course of a treatment. Because of osmotic effects, the amount of fluid which flows out is generally somewhat greater than the amount of fluid which is introduced. Measuring the additional amount of fluid which is removed is of considerable interest in regard to judging the treatment.

In the previously known peritoneal dialysis apparatus, some cases do not carry out a balancing operation, that is to say, they do not determine the additional amount of fluid which is drained off. In some cases, balancing is carried out in a form such that the amount of fluid introduced is metered by means of a balance which is provided with a switching contact, while the amount of fluid which is emptied out is collected in a measuring beaker and the amount thereof must be read off by an operator in order thereby to determine the difference. Apart from the lack of precision which can result from the different nature of the measuring processes (measuring by weight and measuring by volume) and from possible errors in reading off the result, this process and evaluation of the readings are very labour-intensive. Other forms of apparatus avoid this by using volumetric monitoring both of the amount of fluid which is introduced and the amount of fluid which is removed, by means of measuring chambers of constant volume with incorporated level electrodes, but this is liable to trouble for example due to the possibility of foam forming in the measuring chambers, while the fact that the apparatus is fixed on a given filling volume represents a certain limitation. Another known apparatus operates with variable volumetric metering or measurement of the amounts of fluid which flow in and out of the patient, and thus avoids a disadvantage of the previous apparatus, but this process has also not met with practical success because of the high expenditure and the resulting liability to trouble.

The present invention is based on the problem of providing a peritoneal dialysis apparatus which permits the additional amount of fluid which flows out of the patient to be precisely determined by simple technical means and without precision measuring devices. This is achieved by a particularly simple use involving the features recited in the claims.

SUMMARY OF THE INVENTION

According to the invention an abdominal cavity may be rinsed while simultaneously monitoring whether there is a difference in the quantity of fluid going into the patient and coming out of the patient. When the fluid quantity coming out of the patient is equal to the fluid quantity put into the patient further fluid withdrawal is switched into a measuring container to ascertain the fluid excess coming out of the patient.

BRIEF FIGURE DESCRIPTION

Figure 2:
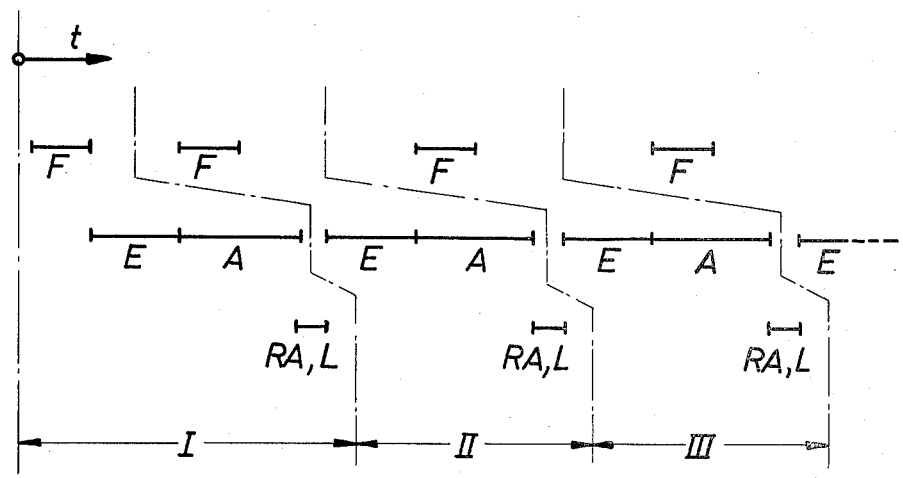

The invention is described hereinafter with reference to the drawings in which:

FIG. 1 shows a diagrammatic view of the functional structure of the peritoneal dialysis apparatus, and FIG. 2 shows a graph representing the manner in which the process proceeds in relation to time.

DETAILED DESCRIPTION OF PREFERRED EXAMPLE EMBODIMENTS AND OF THE BEST MODE OF THE INVENTION

Referring to FIG. 1, the dialysis solution is pumped out of a supply container 2 by means of the tube or hose pump 1 through a heating means 3 into a vessel 4. The heating means 3 may comprise for example a tube coil through which the solution flows and which is disposed in a thermostatically controlled water bed, or another apparatus known for heating infusion solutions. The vessel 4 may be a bag which is vented by way of a sterile filter fitted thereon or another conventional vessel. It is also possible for the functions of the heating means 3 and the vessel 4 to be combined, insofar as the vessel 4 is in the form for example of a flat bag which is arranged between heating plates. Fixing a given amount of solution which is pumped into the vessel 4 can be effected by counting off a given number of revolutions of the tube pump 1, for example by an electronic preselector counter being set in its starting position when the pump is switched on, so that the pump is stopped by the counter when a predetermined number of pulses which can be produced for example by a contact marker actuated by the pump rotor is reached. This or a similar kind of means for fixing the amount of solution which is pumped into the vessel can be used because it is not necessary in this case to have a high degree of absolute precision, but only the possibility of sufficiently reproducing the metering action.

The solution which is pumped into the vessel 4 can be passed to the catheter 6 by opening the tube clamp valve 5, whereby the solution in the vessel 4 can be passed into the abdominal cavity of the patient. When this is done, the solution again passes through the heating means 3 in which it is heated to approximately body temperature. Emptying of the vessel 4 can be automatically detected by a sensor means 7, for example in the form of a light barrier arrangement or ultrasonic barrier arrangement or a capacitive sensor, in order to close the tube clamp valve 5 which is actuated by a solenoid, by means of the electrical signal which is triggered by the above-mentioned sensor means.

So that the fluid which is introduced can run out again, the tube clamp valve 8 is opened, while all the other tube clamp valves 5, 9 and 10 are closed. The fluid which thus runs out passes through the valve 8 into the vessel 11 which is preferably of the same kind as the vessel 4.

The two vessels 4 and 11 are suspended on a simple balance which makes it possible to establish equality in the weights of the two vessels and which provides an electrical switching signal when the two weights are the same. In FIG. 1 the balance is represented by a balance beam 12 which has equal arms and which is mounted at its centre and on the ends of which the two vessels are suspended. As the fluids are to run in and out by virtue of the natural head, the vessels 4 and 11 are suspended at different levels, for example using a rod or a cable 13 for the vessel 11. Another advantageous construction for the balance may provide that the two vessels are secured to the ends of a cable which passes over an easily movable cable roller which takes the place of the balance beam 12. The condition of equal weight of the two vessels is determined by the sensing means 14 which detects the vertical movement of the cable or rod 13 and triggers off an electrical signal when the equal-weight condition is reached, for example by means of a light barrier arrangement or a mechanical contact maker. The sensor means 14 may also be arranged on the balance beam 12 or another suitable position.

When the operation of discharging the fluid from the abdominal cavity of the patient into the vessel 11 through the open valve 8 is begun, at the same time the next operation of filling the vessel 4 is initiated, by the pump 1 being switched on so that it again pumps the predetermined amount of dialysis solution into the vessel 4, by means of the predetermined number of pump revolutions. The pump speed is selected to be of a value such that the operation of filling the vessel 4 is in every case concluded before the fluid flows out of the abdominal cavity into the vessel 1. Consequently, the moment at which the amount of fluid which has flowed out of the abdominal cavity into the vessel is the same as the amount of fluid in the vessel 14 can be determined by the balance with the sensor means 14. Because the pumping operation can be reproduced with a high degree of accuracy, this therefore also establishes identity as between the amount of fluid which was previously introduced into the abdominal cavity, and the amount of fluid which is now discharged into the vessel 11. At this moment, using the signal produced by the sensor means 14, the tube clamp valve 8 is closed in order instead to open the valves 9 and 10. The remaining fluid in the abdominal cavity flows by way of the valve 9 into a measuring vessel 15. The additional amounts of fluid which also occur in the further operating cycles are collected in the measuring vessel 15 so that the total amount of additional fluid which has been drained from the abdominal cavity can be read off at the measuring vessel 15 at the end of the treatment.

The fluid contained in the vessel 11 is emptied through the tube clamp valve 10 when in the open condition into a drain or a collecting container (not shown in the drawing).

After the expiry of a given preselected time which is determined for example by a time clock which is switched on at the same time as the valve 9 is opened and which is such that the vessel 11 is certainly emptied and also the residual fluid in the abdominal cavity has been virtually completely drained from the cavity into the measuring vessel 15, the valves 9 and 10 are closed again and the valve 5 is opened in order to pass the dialysis solution which is ready in the vessel 4 by way of the catheter into the abdominal cavity. The above-described operations are then repeated as described above.

The progress of the steps of the procedure in time are shown diagrammatically in FIG. 2. Each of the operating cycles I, II, III, etc, which are separated by dash-dotted lines, comprises the functional steps F, E, A, RA and L.

In FIG. 2, F denotes filling the vessel 4 with a given number of rotations of the tube pump 1 with the tube clamp valve 5 in a closed condition. The commencement of F is triggered manually in the first cycle (I). Thereafter however, each step F begins when the step E of the preceding cycle is terminated, being triggered by the sensor means 7. The end of step F is determined by reaching the preselected number of revolutions of the tube pump.

E denotes introducing the dialysis solution from the vessel 4 into the abdominal cavity, through the open valve 5 and the catheter 6. The commencement of step E in the first cycle is determined by the end of step F, while in the subsequent cycles it is determined by the end of RA, namely the residue discharge time. The end of step E is determined in every case by operation of the sensor means 7 which indicates that the vessel 4 has been completely emptied.

A denotes discharge of the fluid from the abdominal cavity through the open valve 8 into the vessel 11. The commencement of A is predetermined by the end of step E, that is to say, by the sensor means 7 responding. However, as already mentioned in the preamble, a waiting period may also be interposed between the end of step E and the beginning of step A. This waiting period can be provided by means of a switching clock which is to be set accordingly and which is started at the end of step E and which initiates the step A, only after the expiry of the waiting period, by opening the valve 8, when the valves 5, 9 and 10 are closed. The end of step A is determined by the signal of the sensor means 14 which indicates identity of contents of the vessels 11 and 14.

RA denotes the discharge of the residual fluid from the abdominal cavity through the opened valve 9 (when the valve 8 is closed) into the measuring vessel 15. The commencement of RA is identical to the end of step A, that is to say, it is determined by the sensor means 14 responding. The end of step RA is produced by the signal of a switching clock which was switched on at the same time as the sensor means 14 was actuated.

L denotes emptying of the vessel 11 through the open valve 10 into the drain. As shown in FIG. 2, the commencement and the end of step L may coincide with the commencement and the end of step RA. In principle, step L can also be of greater length, at a maximum up to the commencement of discharge step A.

Although the invention has been described with reference to specific example embodiments, it will be appreciated, that it is intended, to cover all modifications and equivalents within the scope of the appended claims.

What is claimed is:

1. A method for the periodic rinsing of the abdominal cavity of a patient, comprising the following steps:
    (a) supporting a filling vessel (4) and a discharge vessel (11) at opposite ends of a comparing balancing means;
    (b) operatively connecting both vessels through first and second valves (5, 8) to said abdominal cavity;
    (c) filling said filling vessel while said first valve is closed;
    (c) opening the first valve (5) for emptying the filling vessel (4) through said first valve (5) into said abdominal cavity;
    (e) closing the first valve (5), opening the second valve (8) and draining the abdominal cavity into said discharge vessel (11) while simultaneously refilling said filling vessel (4);
    (f) closing the second valve (8) in response to a balanced condition as sensed from said comparing balancing means when the filling vessel and the discharge vessel hold the same quantity of liquid;

(g) continuing the draining into a measuring vessel; and (h) emptying the discharge vessel, wherein said measuring vessel provides a measure for any liquid excess being drained from said cavity in addition to the liquid supplied through said filling vessel.

2. The method of claim 1, comprising using as said comparing balancing means a balancing beam, connecting said filling vessel and said discharge vessel to opposite ends of said balancing beam so that said vessels are located at different elevational levels, and controlling the operation of valve means (5) in response to the empty condition of said filling vessel (4) and of further valves (8, 9, 10) in response to the balanced condition of said balancing beam.

3. The method of claim 2, comprising locating the abdominal cavity (6) at an elevational level between said filling vessel (4) and said discharge vessel (11), whereby the filling and emptying of the abdominal cavity may be accomplished substantially by gravity flow.

* * * * *